US 7,598,019 B2

(12) United States Patent
Steiner et al.

(10) Patent No.: US 7,598,019 B2
(45) Date of Patent: Oct. 6, 2009

(54) METHOD FOR CLEAVAGE OF LABILE FUNCTIONAL GROUPS FROM CHEMICAL COMPOUNDS

(75) Inventors: Ulrich Steiner, Constance (DE); Dominik Woll, Constance (DE); Stefan Walbert, Constance (DE)

(73) Assignee: Universitat Konstanz, Constance (DE)

( * ) Notice: Subject to any disclaimer, the term of this patent is extended or adjusted under 35 U.S.C. 154(b) by 0 days.

(21) Appl. No.: 10/934,102

(22) Filed: Sep. 2, 2004

(65) Prior Publication Data

US 2005/0255403 A1     Nov. 17, 2005

(30) Foreign Application Priority Data

Mar. 4, 2002   (DE)  ................................ 102 09 203
Mar. 4, 2003   (WO)  ..................... PCT/EP03/02208

(51) Int. Cl.
    *G03F 7/00*           (2006.01)
    *G03F 7/004*         (2006.01)
(52) U.S. Cl. ...................... 430/311; 430/270.1; 430/394
(58) Field of Classification Search ............... 430/270.1, 430/311, 394
See application file for complete search history.

(56) References Cited

U.S. PATENT DOCUMENTS 4,487,870 A     12/1984    Bartz (Continued)

FOREIGN PATENT DOCUMENTS

CA          2362699 A1 *   9/2000

(Continued)

OTHER PUBLICATIONS

Liu et al , "Application of UV-Curable Diazoresin .I. Immobilization of Glucose Oxidase into PVA in the presence of UV-Sensitive Diazoresin and Sensitizers", J. of Applied Polymer Science, vol. 40 (1990). 2161-2171.*

(Continued)

*Primary Examiner*—Amanda C. Walke
(74) *Attorney, Agent, or Firm*—Joshua King; Graybeal Jackson LLP

(57) ABSTRACT

The present invention provides a method for cleavage of labile functional groups from molecules by the action of electromagnetic radiation, wherein the molecules are contacted with a chemical compound whose triplet state is energetically higher than the triplet state of the labile functional group, and are subsequently exposed to electromagnetic radiation. Further, the invention provides a method for preparing DNA chips by spatially addressed, light-controlled nucleotide synthesis on solid substrates, said method comprising the following steps: a) reacting the unprotected terminal 3' or 5' hydroxy group of a nucleoside and/or of a nucleotide arranged on the solid substrate under usual conditions with a photolabile protective group and optionally purifying the reaction product, b) applying a solution, suspension or dispersion of a chemical compound, whose triplet state is energetically higher than the triplet state of the photolabile protective group, to the surface of the carrier, said surface comprising the nucleotides and/or nucleosides modified in step a); c) irradiating, in a spatially selective manner, the surface of the carrier treated in step b) with electromagnetic radiation in the UV/VIS range with simultaneous, spatially selective release of a reactive OH group and subsequently reacting it with a nucleoside and/or nucleotide comprising a 5' or 3'OH group, said nucleoside and/or nucleotide being further provided with a photolabile functional group. Moreover, the present invention provides a chemical composition comprising a molecule having a labile functional group, as well as a chemical compound whose triplet state is higher than the triplet state of the labile functional group, and it describes the use of the chemical composition for preparing DNA chips.

17 Claims, 4 Drawing Sheets

U.S. PATENT DOCUMENTS

| | | | |
|---|---|---|---|
| 4,992,547 | A | 2/1991 | Berner et al. |
| 5,763,599 | A | 6/1998 | Pfleiderer et al. |
| 6,552,182 | B2 * | 4/2003 | Stengele et al. ............ 536/25.3 |
| 6,867,250 | B1 | 3/2005 | Gupta et al. |
| 7,235,282 | B2 | 6/2007 | Tchapian et al. |
| 2003/0166738 | A1 | 9/2003 | Ishizawa et al. |

FOREIGN PATENT DOCUMENTS

| | | | |
|---|---|---|---|
| CH | 693202 A | | 4/2003 |
| DE | 4444956 A1 | | 6/1995 |
| DE | 4444996 A1 | | 6/1996 |
| DE | 19620170 A1 | | 11/1997 |
| DE | 10011400 A1 | | 5/2000 |
| DE | 19938092 A1 | | 2/2001 |
| EP | 1046421 A2 | | 10/2000 |
| EP | 1065280 A2 | * | 1/2001 |
| EP | 1106603 A2 | * | 6/2001 |
| JP | 07070220 A | | 3/1995 |
| WO | WO 9618634 A2 | * | 6/1996 |
| WO | WO 9744345 A1 | * | 11/1997 |
| WO | 0035931 A2 | | 6/2000 |
| WO | WO 01/32671 A1 | | 5/2001 |
| WO | WO01/32671 A1 | | 5/2001 |
| WO | 2001090054 A2 | | 11/2001 |
| WO | 03074542 A2 | | 9/2003 |
| WO | WO 03/074542 A3 | | 9/2003 |
| WO | 2004001033 A2 | | 12/2003 |

OTHER PUBLICATIONS

International Preliminary Examination Report, PCT/EP2003/002208, Oct. 24, 2005.

LeProust, Eric, et al., Digital Light-Directed Synthesis. A Microarray Platform That Permits Raptid Reaction Optimization on a Combinatorial Basis, J. Combinatorial Chemistry (2000), 2 (4), 349-354 (XP001058977).

Quian, Xuhong, et al., Interaction of Naphthyl Heterocycles with DNA: Effects of Thiono and Thio Groups, J. Chem Society, Perkin Trans., (2000), 2(4), 715-718 (XP002252650).

Slocum, Gregory H., et al., Photochemistry of Naphthylmethyl Halides. Direct and Sensitized Paths to Homolythic Heterolythic Carbon-Halogen Bond Cleavage, J. of Organic Chem. (1984), 49 (12) 2177-2185 (XP002252651).

LeProust, Eric, et al., Digital Light-Directed Synthesis. A Microarray Platform that Permits Rapid Reaction Optimization on a Combinatorial Basis, XP-001058977, J. Comb. Chem., pp. 349-354, 2000.

McGall, Glenn H., et al., The Efficiency of Light-Directed Synthesis of DNA Arrays on Glass Substrates, J. American Chemical Society, vol. 119, No. 22, Jun. 4, 1997.

Pirrung, Michael C., et al., Proofing of Photolithographic DNA Synthesis with 3', 5'-Dimethoxybenzoinyloxycarbonyl-Protected Deoxynucleoside Phosphoramidites, XP-000916248, American Chemical Society, 1998.

Qian, Xuhong, et al., INteraction of Naphthyl Heterocycles with DNA: Effects of Thiono and Thio Groups, XP-002252650, The Royal Society of Chemistry, pp. 715-718, 2000.

Dr. Hans Rudolf Christen, Grundlagen der organischen Chemie (Basics of Organic Chemistry), pp. 468-469, English Translation of relevant paragraph cited in Office Action, 1982.

Singh-Gasson, Sangeet, et al., Maskless Fabrication of Light-Directed Oligonucleotide Microarrays Using a Digital Micromirror Array, XP-002126301, Nature Biotechnology, vol. 17, 1999.

Slocum, Gregory H., et al., Photochmistry of Naphthylmethyl Halides. Direct and Sensitized Paths to Homolytic and Heterolytic Carbon-Halogen Bond Cleavage, XP-002252651, J. Org. Chem., 1984.

Office Action from German Patent Office with English Translation and English Translation of Response to Office Action, 2002.

S.P.A. Fodor, DNA Sequencing Massively Parallel Genomics, Science 277 (1997) 393.

G.H. Mcgall et al., "New Insight into the Mechanism of Base Propenal Formation during Bleomycin-Mediated DNA Degradation", J. Am. Chem. Soc. 1992, 114, 4958-4967.

P. E. Nielsen et al., "DNA Binding and Photocleavage by Uranyl(VI) (UO22+) Salts", J. Am. Chem. Soc. 1992, 114, 4967-4975.

International Search Report, International Application No. PCT/EP03/06588, Jan. 13, 2004.

U.S. Appl. No. 60/361,562, filed Mar. 4, 2002.

A. Banerjee et al., Photoreleasable Protecting Groups Based on Electron Transfer Chemistry, Donor Sensitized Release of Phenacyl Groups from Alcohols, Phosphates and Diacids, Tetrahedron 55 (1999) 12699-12710.

S.P.A. Fodor et al., Multiplexed biochemical assays with biological chips, Nature 364 (1993) 555.

D.J. Lockhart, E.A. Winzeler, Genomics, gene expression and DNA arrays, Nature 405 (2000) 827.

V.N.R. Pillai, Photolytic Deprotection and Activation of Functional Groups, in: Organic Photochemistry, vol. 9, ed. A. Padwa (Marcel Dekker, New York and Basel, 1987), p. 225 et seq.

J.E.T. Corrie, D.R. Trentham, Caged Nucleotides and Neurotransmitters, in: Biological Applications of Photochemical Switches, in: Bioorganic Photochemistry Series, vol. 2, ed. Harry Morrison (Wiley Interscience, 1993), p. 243 et seq.

S.P.A. Fodor et al., Light-Directed, Spatially Addressable Parallel Chemical Synthesis, Science 251 (1991) 767.

U.S. Appl. No. 11/019,938, filed Dec. 21, 2004, titled, "Method For Cleaving of Labile Functional Groups From Chemical Compounds," now abandoned.

* cited by examiner

METHOD FOR CLEAVAGE OF LABILE FUNCTIONAL GROUPS FROM CHEMICAL COMPOUNDS

CROSS-REFERENCE TO RELATED APPLICATIONS

The present application claims priority under all appropriate statutes and provisions from: International Application Number PCT/EP03/02208, International Filing Date Mar. 4, 2003; German Application Number 102 09 203.6, filed Mar. 4, 2002; and, U.S. provisional patent application Ser. No. 60/361,562, filed Mar. 4, 2002, which applications are incorporated herein by reference in their entirety.

The present invention relates to a method for cleavage of labile functional groups from molecules by the action of electromagnetic radiation as well as to a method for preparing DNA chips by spatially addressed, light-controlled nucleotide synthesis on solid substrates, further to a chemical composition as well as to the use of said chemical composition in preparing DNA chips.

Easy cleavage of functional groups from molecules plays an important role in many fields of chemistry and biology, for example, in the construction of larger chemical units, such as in the synthesis of polymers, natural products, etc. In doing so, particularly reactive groups which may affect or disturb the respective intended linking of two molecules by undesired side reactions, are temporarily "masked" or protected in a selective manner by chemically or physically cleavable functional protective groups to prevent them from participating in the desired linking reaction.

The use of large combinatorial libraries of binding partners, immobilized on a substrate, of the biomolecules provided in solution is of great advantage in a comparative study of molecular recognition between biomolecules of the same or different structural classes.

To the person skilled in the art, the term "biomolecules" designates compounds of the classes of nucleic acids and their derivatives, proteins, peptides and carbohydrates.

This principle of mutual molecular recognition is applied, in particular, in the selective construction of polynucleotides from nucleoside units and/or oligonucleotide units. The selective construction of polynucleotides, in turn, is of decisive importance in preparing DNA chips having a high density ("high-density DNA-chip") of polynucleotides arranged thereon.

DNA chips, i.e. so-called microarrays of fields on a glass or polymer substrate of immobilized DNA or randomly selected oligonucleotides functioning as super-multiplex probes for molecular recognition by hybridization, (S. P. A. Fodor, Science 277 (1997) 393, DNA Sequencing Massively Parallel Genomics) have long since been employed, for example, in medicine and in pharmaceutical research.

In said fields, DNA chips again play an important role in genetic analysis and diagnostics. The most wide-spread technique for preparing such DNA chips is the so-called spatially addressed, parallel, light-controlled oligonucleotide synthesis on solid substrates (see e.g. S. P. A. Fodor et al, Nature 364 (1993) 555, Multiplexed Biochemical Arrays with Biological chips) using photolabile protective groups, i.e. protective groups for reactive functionalities of nucleoside or nucleotide units which can be selectively cleaved again under the action of, in most cases, UV light of a certain wavelength, so that the protected functionalities are available again for further reaction.

In this case, the afore-mentioned, so-called photolithographic technique serves to prepare said DNA chips. For this purpose, the synthetic construction of the desired oligonucleotide chains on the substrate is controlled by suitable labile protective groups, which release the linkage site for the respective next nucleotide, for example, upon exposure to light. These protective groups have hitherto been preferably photolabile. With the help of these photolabile protective groups, a combinatorial strategy can be developed by means of spatially selective exposure to light, said strategy allowing to generate extremely dense, spatially addressable microarrays of oligonucleotides whose number increases exponentially with the number of synthesis cycles ("split and pool"). For a currently achievable surface area of each element of less than 50 $(\mu m)^2$, more than $10^6$ probe fields may be theoretically arranged on 1 $(cm)^2$. Light exposure has hitherto been effected with the help of microrirror arrays (S. Singh-Gasson, et al, Nature Biotechn. 17 (1999) 974, Maskless Fabrication of Light Directed Olignucleotide Microarrays using a Digital Micromirror Array), as used in digital projection technology. This saves the time- and cost-intensive preparation of exposure masks and has made it possible to prepare the DNA chips more rapidly using said photolithographic technique.

Currently employed photolabile protective groups do not yield satisfactory results in terms of the error rate of the thus-synthesized DNA chips (D. J. Lockheart and E. A. Winseler, Nature 405 (2000) 827, Genonics, Gene expression and DNA arrays). Cleavage of the protective groups does not take place sufficiently completely; moreover, there are disturbing side reactions with undesired reaction products, so that a large number of the oligonucleotides on the DNA chips can not be used.

A central point in photolithographic synthesis consists in the use of the photolabile protective groups, which can be used in numerous chemical variants in organic and bioorganic chemistry (V. N. R. Pillay, Photolithic Deprotection and Activation of Functional Groups; in: Organic Photochemistry, Vol. 9 ed. A. Padwa (Marcel Dekker, New York and Basel, 1987), page 225 et seq.). The most common protective groups are photolabile protective groups on the basis of the 2-nitrobenzyl group. (J. E. T. Correy and E. R. Trenton, Caged Nucleotides and Neurotransferters; in: Biological Applications of Photochemical Switches, in: Bioorganic Photochemistry Series, Vol. 2 ed. Harry Morrison (Wiley Interscience, 1993), page 243 et seq.).

In the preparation of DNA chips, for example when protecting the terminal 5'-OH group in the oligonucleotide construction from the 3' end to the 5' end or from the 5' end to the 3' end, the preferred protective group among the protective groups of the 2-nitrobenzyl type has hitherto been, above all, the MeNPOC (α-methyl-nitropiperonyloxycarbonyl) protective group which has long since been the standard protective group in DNA chip preparation (S. P. A. Fodor, et al, Science 251 (1991), 767, Light Directed, Spatially Adressible Parallel Chemical Synthesis).

A disadvantage of this type of protective groups is the formation, upon irradiation, of the aromatic nitrosoketone which represents a very reactive leaving group. This results in undesired consequent reactions which often cause errors in the nucleotide structure of the resulting oligonucleotide or polynucleotide.

Use has recently been made also of the DMBOC group (3',5'-dimethoxy benzoinyloxycarbonyl) as a protective group (M. C. Pirrung et al, J. Org. Chem. 63 (1998), 241, Proofing of Photolithographic DNA synthesis with 3',5'-Dimethoxybenzoinyloxycarbonyl-protected Deoxynucleosidephosphoramidites) in selective polynucleotide synthesis. The cleavage of the DMBOC protective group produces a benzofurane derivative whose intense fluorescence may be used, for example, as an indicator of the progress of the photoreaction.

Both of the presently known photolabile protective groups require irradiation times of several minutes under the usual irradiation intensities with the 365 nm line of a mercury lamp, in order to react quantitatively.

Further, 2-(2-nitrophenyl)-ethoxycarbonyl compounds are known in the preparation of DNA chips, wherein the protective groups are cleaved as 2-nitrostyrene derivatives (German Patent Nos. 44 44 996 and 196 20 170, and U.S. Pat. No. 5,763,599). Also, these compounds are somewhat less prone to error than the aforementioned compounds in terms of disturbing side reactions due to cleavage of generally somewhat less reactive 2-nitrostyrenes.

Therefore, it was an object of the present invention to find a method wherein the cleavage of labile groups was considerably reduced in terms of reaction time of the cleavage reaction and allowing the cleavage reaction to be optimized in terms of its yield. A further object was to reduce the risk of undesired side reactions during cleavage of the labile protective group.

The above object of the present invention is achieved in that the method, according to the invention, for cleavage of labile functional groups from molecules comprises the following steps:
a) selecting a suitable chemical compound whose triplet state is energetically higher than or very similar to the triplet state of the labile functional group;
b) contacting it with the molecules comprising said labile functional groups;
c) exposure to electromagnetic radiation, with the sequence of steps b) and c) being optional.

The method according to the invention allows to achieve excitation of the triplet state of the selected chemical compound according to the invention and to transfer the electromagnetic radiation thus absorbed by the selected chemical compound (also termed as "sensitizer") to the labile functional group via a triplet-triplet transition, which labile functional group may be subsequently cleaved in an efficient and rapid manner.

This finding is particularly surprising, especially in the synthesis of polymers, more specifically biopolymers like nucleic acids, peptides, carbohydrates and the like, which are instable when brought together with the radicals which are generated in the method according to the invention during the excitation of the sensitizer. The sensitizer in its excited state is a radical. It is well known in the art that many polymers, especially biopolymers are instable when reacting with or brought in contact with radicals. Especially nucleic acids will react with radicals via a radical substitution at the position of the bases or by breaking nucleic acids at its sugar positions in small fragments. The cleavage of a nucleic acid yields to free nucleic bases (adenine, cytosine, guanine and thymine) which are the reaction product of the radicalic substitution of the bases of nucleic acid. The scission of nucleic acids leads to a large variety of different nucleic acid fragments thus not yielding the desired biopolymer. (See e.g. G. H. McGall et al., "New Insight into the Mechanism of Base Propenal Formation during Bleomycin-Mediated DNA Degradation", J. Am. Chem. Soc. 1992, 114, 4958-4967 and P. E. Nielsen et al., "DNA Binding and Photocleavage by Uranyl(VI) ($UO_2^{2+}$) Salts", J. Am. Chem. Soc. 1992, 114, 4967-4975).

Similar reactions are known from other biopolymers like e.g. oligopeptides, proteins and sugars (carbohydrates).

Therefore, the method according to the invention provides a surprising finding that those polymers, especially biopolymers, being destroyed during or after formation can be synthesized according to the method of the invention by using radicalic sensitizers, which overcomes a long prejudice in the art.

The term "very similar triplet state" as used herein means that "very similar" comprises an energy range around the triplet state which is a multiple n of the average thermal energy RT with an order of magnitude of ca. 2.5 kJ of the triplet state of the chemical compound according to the invention, wherein n=8, preferably n=4.

The sequence of steps b)-c) makes particularly good use of the radiation energy, since, in addition to the conventional reaction of the photolabile group, sensitizing via triplet-triplet energy transfer is also used.

The contacting is effected by methods essentially known to the person skilled in the art. Both compounds, i.e. the molecules comprising the labile functional groups and the chemical compound according to the invention (also referred to in the following as "sensitizer or sensitizer compound"), are advantageously present in the same phase.

Depending on the selection of the functional protective group and of the corresponding sensitizer compound, their respective absorption maxima for electromagnetic radiation are determined. This also allows a deliberate selection of the corresponding wavelength of electromagnetic radiation from the electromagnetic wavelength spectrum.

However, cleavage is also successful where only the sensitizer compound is activated by said electromagnetic radiation, i.e. for a sequence of steps c)-b) of the method according to the invention. The sensitizer compound then transfers its triplet energy very efficiently to the functional protective group. This advantageously results in molecules being subjected to a cleavage reaction which would otherwise be unsuitable for such reactions, which are provided with functional protective groups and which would be destroyed, for example, by electromagnetic radiation having a defined wavelength initiating cleavage. This is effected by selecting the suitable sensitizer compound and irradiating it at an uncritical wavelength which does not destroy the molecules and only activates the sensitizer compound which subsequently transfers said energy, by means of said triplet-triplet transfer, to the sensitive molecules, so that the functional groups can be cleaved nevertheless. For example, the sensitizer compound can be activated by prior radiation with a laser or other high-energy radiation, such as X-ray, electron or particle beams, such as α or γ-rays.

Also, a further advantageous embodiment allows steps b) and c) to be carried out simultaneously.

Preferably, the labile group is photolabile, so that the method according to the invention can be easily employed, in particular, in known methods for the preparation of DNA chips. The electromagnetic radiation is preferably within the wavelength range of UV/VIS radiation (210-450 nm). This allows the method according to the invention to be used preferably in the preparation of DNA chips using conventional mercury vapor lamps.

Particularly advantageously, the singlet state of the chemical compound is as high as or lower than the singlet state of the labile functional group. Under these prerequisites, the wavelength, and thus the energy of the incident light may be shifted within a certain range, i.e. to a so-called "window" of the electromagnetic spectrum, in which the side reactions to be expected, in particular in preparing the DNA chips, can be minimized.

Particularly preferably, the triplet-singlet energy gap of the chemical compound is smaller than the triplet-singlet energy gap of the labile functional group. The chemical compound preferably still has a high triplet-formation quantum yield $\phi_T$ near the maximum possible value of 1.

The object of the above invention is further achieved by a method for preparing molecular libraries containing biomolecules, in particular for preparing DNA chips and peptide chips as well as their analogous and mimetic forms, by means of spatially addressed light-controlled synthesis on solid substrates, said method comprising the following steps:

a) reacting the unprotected terminal 3' or 5' hydroxy group of a nucleoside and/or nucleotide arranged on the solid substrate or a nucleic acid analog or a —COOH or amino group of a suitable peptide under usual conditions known to the person skilled in the art using a photolabile protective group or reacting an —OH, —COOH, —NHR group, wherein R=H, alkyl, aryl, aralkyl with a unit comprising a photolabile protective group and optionally purifying the reaction product;

b) applying a chemical compound, whose triplet state is energetically higher than or very similar to the triplet state of the photolabile protective group to the surface of the carrier, said surface comprising the nucleotides and/or nucleosides or nucleic acid analogs or peptides or peptide mimetics modified in step a);

c) irradiating, in a spatially selective manner, the surface of the carrier treated in step b), with electromagnetic radiation in the UV/VIS range;

d) reaction with a nucleoside and/or nucleotide, wherein a free 5' or 3'OH group is protected using a photolabile group, or using a corresponding suitable peptide or with a suitable amino acid;

e) optionally repeating steps b) to d).

The compound is applied by common methods, such as knife coating, atomizing, spraying, dropwise addition, etc., wherein the chemical compound may be added in a pure state, in solution, as a suspension or as a dispersion.

This results in an increase in the overall absorption of electromagnetic radiation, since the light absorbed by the sensitizer has a very effective impact on the cleavage reaction due to the transfer of its triplet energy to the labile protective group. At a given radiation intensity, cleavage, therefore, takes place faster in the presence of the sensitizer.

Of course, this method is equally advantageous for the synthesis of polypeptides as for that of other molecules, like carbohydrates and other biopolymers.

Further, the object of the present invention is achieved by providing a chemical composition which comprises a molecule having a labile functional group, as well as a chemical compound whose triplet state is energetically higher than or very similar to the triplet state of the labile functional group.

The combination of two different compounds having different triplet states, one of said triplet states being higher than or very similar to the other triplet state, allows a virtually loss-free transfer of triplet excitation energy from one compound to the labile functional group, which picks up said energy and is then more easily cleaved without itself having to be excited by to electromagnetic radiation.

The functional group is preferably a photolabile group, since the possibility of the available wavelengths or of the radiation waves is easier to provide. However, use may also be made of all other groups which can be irradiated with other electromagnetic radiation, for example IR radiation, or radiation of a longer or of a shorter wavelength.

The labile group, in particular the photolabile group, is preferably selected from the group consisting of NPPOC, MeNPOC, MeNPPOC, PhNPPOC, DMBOC, NPES, NPPS and their substituted derivatives, substituted and unsubstituted, condensed and uncondensed 2-(nitroaryl)ethoxycarbonyl or -thiocarbonyl compounds, substituted and unsubstituted, condensed and uncondensed 2-nitrobenzyl-, 2-nitrobenzyloxycarbonyl- or thiocarbonyl compounds, substituted and unsubstituted, condensed and uncondensed 2-(nitroheterocycloaryl)ethoxycarbonyl, or -thiocarbonyl compounds, as well as substituted and unsubstituted, condensed and uncondensed 2-(nitroheterocycloalkyl)ethoxycarbonyl/thiocarbonyl compounds, substituted and unsubstituted 2-nitro-N-methylanilincarbonyl- or -thiocarbonyl derivatives.

The aforementioned abbreviations have the following meanings herein:

NPPOC 2-(2-nitrophenyl)propyloxycarbonyl

MeNPPOC 2-(3,4-methylenedioxy-2-nitrophenyl) propyloxycarbonyl

MeNPOC 2-(3,4-methylenedioxy-2-nitrophenyl) oxycarbonyl

DMBOC Dimethoxybenzoinylyloxycarbonyl

NPES 2-(2-nitrophenyl)ethylsulfonyl

NPPS 2-(2-nitrophenyl)propylsulfonyl

PhNPPOC 2-(5-phenyl-2-nitrophenyl)-propyloxycarbonyl

The nucleoside bases guanine, thymine, cytosine and adenosine are represented by their usual abbreviations G, T, C and A.

The chemical compound preferably contains the structural motive

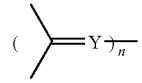

wherein Y=O, S, N, Se or Te, n=1 or 2, C is part of an aromatic, heteroaromatic or condensed aromatic or heteroaromatic system and wherein, in case n=2, the aromatic, heteroaromatic or condensed aromatic or heteroaromatic system may be the same or different.

In particular, the presence of conjugated n-systems or conjugated double bonds is advantageous.

Particularly preferably, use is made of benzophenone, xanthone and thioxanthone derivatives, like e.g. thioxanthen-9-one (thioxanthone), alkylthioxanthen-9-ones, as for example isopropylthioxanthen-9-one, 2-ethylthioxanthen-9-one, 2-chloro-thioxanthen-9-one, 1,4 dimethoxythioxanthen-9-one.

The structural motive according to the invention allows efficient intersystem-crossing into the triplet state, a long triplet life of more than 0.6 microseconds (µs), in particular of more than 1 microsecond (µs). Moreover, it has the effect that the chemical compound is, for the most part, chemically stable in the triplet state, so that the compound is very unreactive in the triplet state.

Of course, the chemical compound according to the invention can be employed not only alone, but also as an excited or non-excited dimer, oligomer, multimer, associate, as a complex with compounds comprising an element of the Periodic Table, preferably a metal or a semimetal. Of course, two or more different compounds according to the invention may also be employed without departing from the scope of the invention.

Use is preferably made of solutions comprising, based on the solvent employed, 0.001 to 5 weight-%, particularly preferably between 0.005 and 0.05 weight-% of the chemical compound according to the invention.

In many cases, an amount of more than 5 weight-% of the chemical compound (sensitizer) according to the invention leads to unwanted chemical reactions. One reaction is the reaction between an excited sensitizer and a non-excited sensitizer molecule. The sensitizer is a radical in its excited state. Especially in the case when sensitizers comprising condensed aromatic systems are used, the sensitizer radical interacts with non-excited sensitizer molecules, leading to H-abstraction and further to dimerization, oligomerization, polymerization etc.

The other reaction often encountered in the reaction of the excited sensitizer with the molecule comprising the functional group, in particular during the synthesis of oligonucleotides and DNA sequences, and may destroy them. Therefore, lower concentrations are preferred in most cases. The precise selection of the suitable concentration is easy to determine by the person skilled in the art using few prior experiments known per se to the person skilled in the art.

The chemical composition according to the invention is preferably used for preparing DNA chips, since it allows an easy transfer of energy between the triplet state of the sensitizer compound and of the photolabile protective group and thus the photochemical cleavage reaction can be initiated in a particularly rapid and complete manner.

According to the invention, the term "nucleotide" means both polynucleotides comprising two to 10 nucleosides which are linked with each other via both 3'-5' and 5'-3' phosphoric acid ester bonds. However, the nucleotides according to the invention also comprise polynucleotides consisting of more than 10 nucleoside units.

The methods according to the invention are not suitable for DNA- and RNA nucleotide synthesis. Of course, the synthesis of polynucleotides from nucleic acid analogs, such as PNA, LNA or chimeric forms thereof with DNA, RNA or nucleic acid analogs is also possible. Further, polypeptides may also be prepared thereby.

The methods according to the invention are particularly suitable to carry out an automated method. Such automated method is preferably embodied as a parallel synthesis for preparing a nucleotide library, wherein the chemical compounds employed or the labile protective groups may be selectively or randomly chosen.

In a further embodiment, the present invention comprises a kit containing some or all reagents and/or auxiliaries and/or solvents and/or a working instruction for carrying out a method according to the invention in one spatial unit, said kit comprising at least one or more selected nucleotides, which preferably comprise a free 5'-hydroxy function and a protected 3'-hydroxy function, or a free 3'-hydroxy function and a protected 5'-hydroxy function. In a further embodiment, said kit comprises corresponding peptides and/or amino acid derivatives having a protected amino group and a free carboxylic group, or vice versa.

According to a still further embodiment, the present invention comprises the use of the method according to the invention and/or of the aforementioned kit for preparing of oligonucleotides or nucleic acid chips, preferably for the automated manufacture of oligonucleotides or nucleic acid chips.

Further advantages and embodiments of the invention are evident from the description and from the attached Figure.

It is understood that the aforementioned features, and the features to be explained in the following, are usable not only in the respective specified combination, but also in other combinations or alone, without departing from the scope of the present invention.

The invention is explained hereinafter with reference to a Figure and to some non-limiting embodiment examples.

Figure 1:
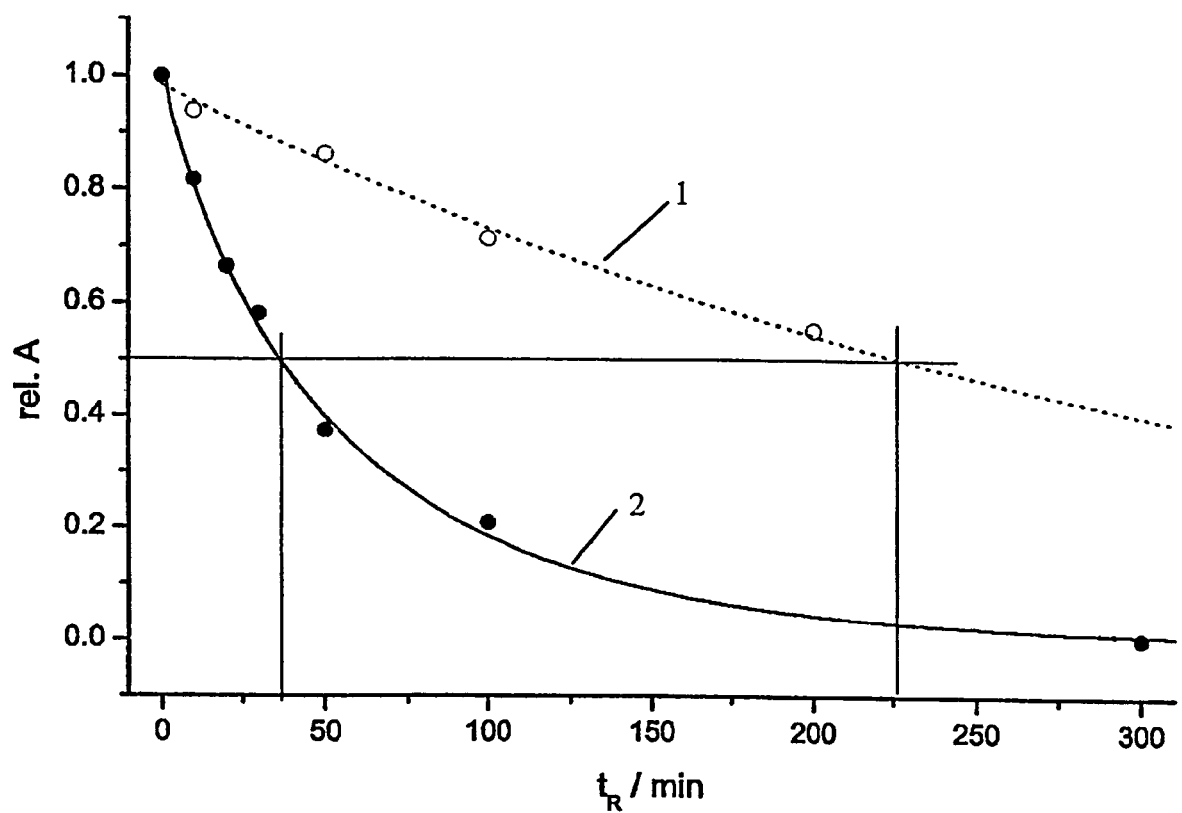
FIG. 1 shows the reaction rate of the cleavage reaction in a method according to the invention.

In FIG. 1 the abscissa indicates the relative concentration of the compound provided with a protective group, as determined by HPLC, plotted as a function of the radiation time ($t_R$/min) in minutes (ordinate). Graph 1 represents the radiation of compound T07 (2-(5-iodo-2-nitrophenyl)propylthymidine-5'-yl-carbonate) (0.096 mM) at 366 nm and an intensity of $4.98 \times 10^{-3}$ W/cm$^{-2}$. Graph 2 shows the radiation of compound T02 (2-(2-chloro-6-nitrophenyl)ethylthynidine-5'-yl-carbonate) (0.091 mM) at the same wavelength and an intensity of $6.39 \times 10^{-3}$ W/cm$^{-2}$ in the presence of thioxanthone (0.113 mM) as the sensitizer in ammnonia-saturated acetonitrile. Although the light intensity in the case of Experiment 2 is only 25% higher, the reaction rate is six times as high.

Figure 2:
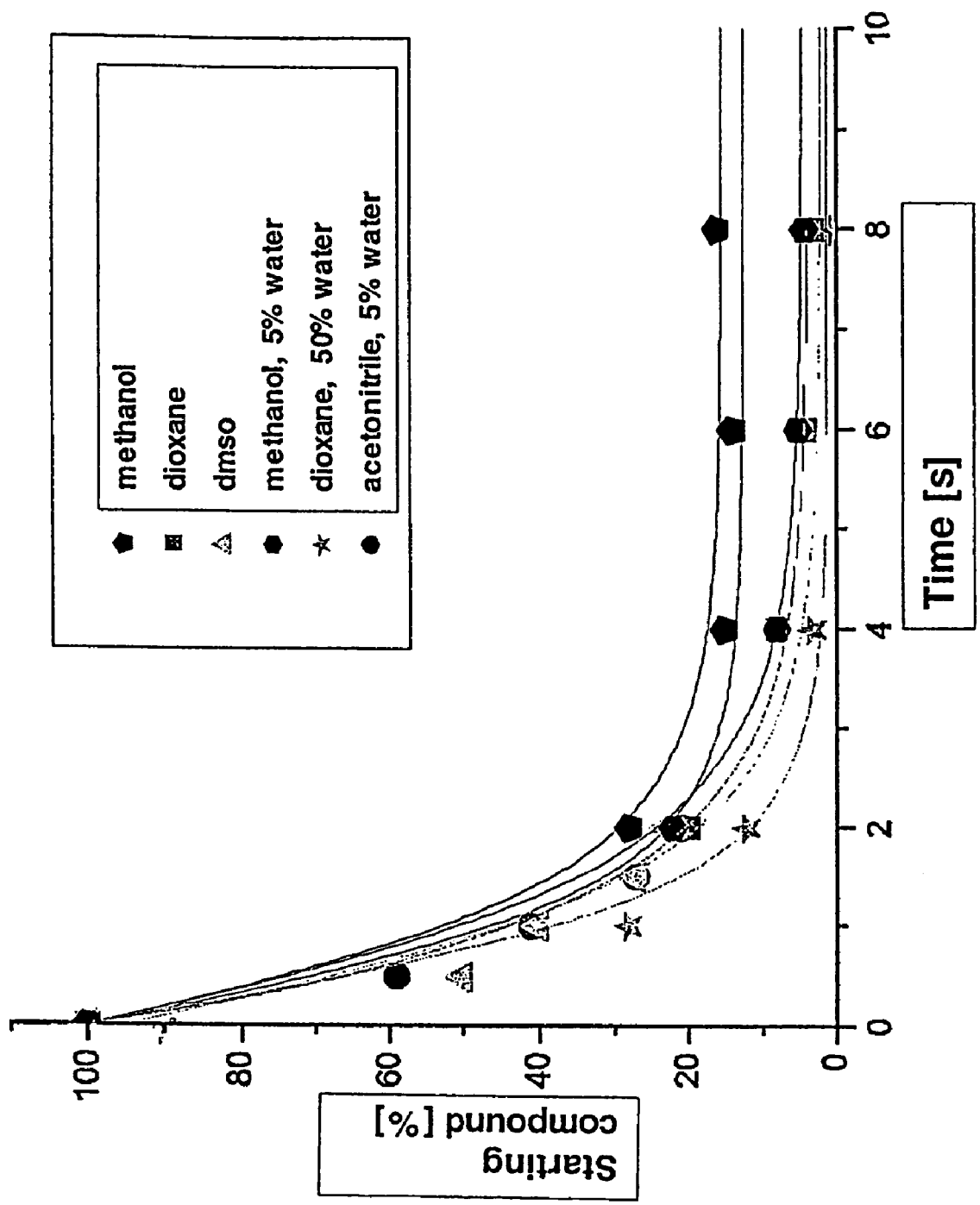
FIG. 2 shows the influence of the solvent upon irradiation of 5'-5PhNPPOC-T in solution.

FIG. 2 shows the influence of the solvent where irradiation of 5'-5PhNPPOCT-T takes place. The graphs represent the percentage of the initial starting compound (educt) versus reaction time in seconds. As can be seen from FIG. 2, the rate of cleavage of the protective group of 5'-5PhNPPOC-T decreases in the order of: dioxane with 50% water>DMSO>dioxane>methanol with 5% water>acetonitrile with 5% water>pure methanol. The reaction rate reaches a maximum value in a mixture of dioxane with 50% water. As a conclusion, strong polar solvents yielded the best results.

Figure 3:
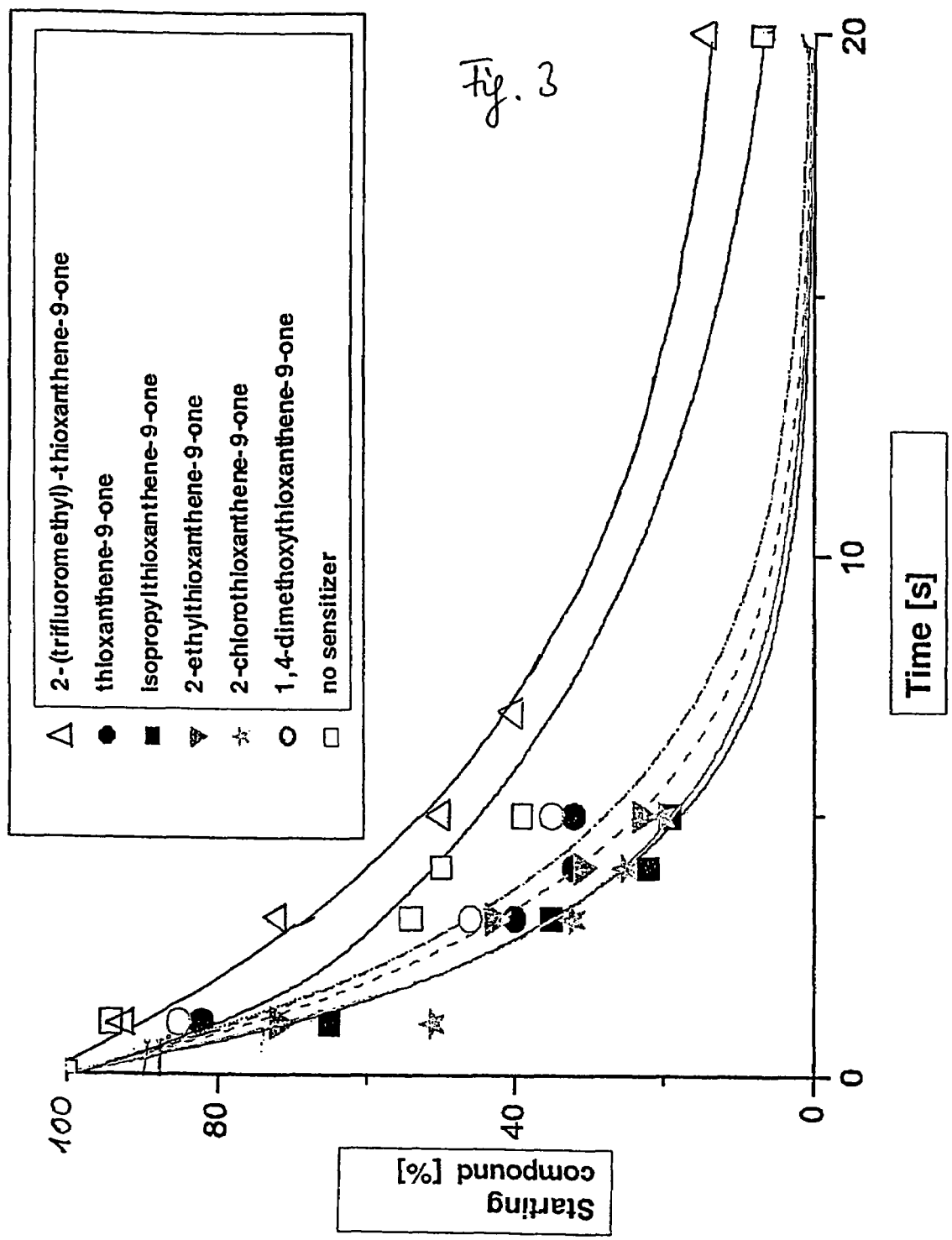
FIG. 3 shows the influence of different sensitizers upon irradiation of 5'-NPPOC-T in solution.
Figure 4:
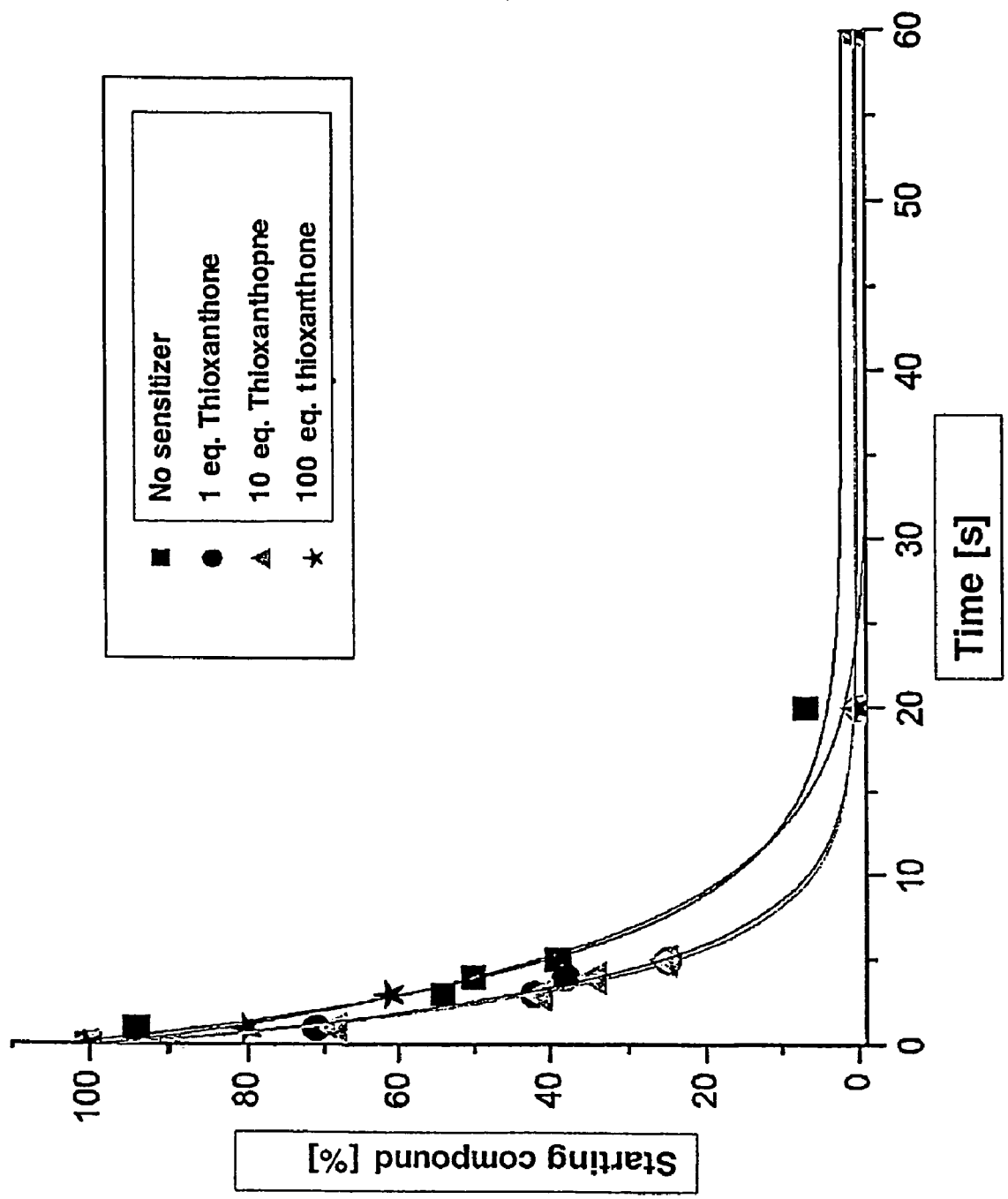
FIG. 4 shows the influence of the concentration of the sensitizer upon irradiation of 5'-NPPOCT in solution.

FIGS. 3 and 4 show the influence of the sensitizer with respect to its chemical nature (FIG. 3) and with respect to its concentration (FIG. 4).

FIG. 3 shows the rate of the deprotection reaction (cleavage of a protecting group) as a function of the decrease of percentage of the starting compound versus the time. As can be seen from FIG. 3, the isopropyl derivative of tioxanthene-9-one yields the best results with respect to the reaction rate. The order of reaction rate is as follows:

Isopropylthioxanthen-9-one, 2-chlorothioxanthen-9-one, 2-ethylthioxanthen-9-one, thioxanthen-9-one together with 1,4-dimethoxythioxanthen-9-one and 2-(trifluoromethyl) thioxanthen-9-one. It has to be noted that the trifluoromethyl derivative causes an even slower reaction than a reaction upon irradiation without the presence of a sensitizer.

FIG. 4 shows the influence of the concentration of a sensitizer upon the reaction rate when irradiating 5'-NPPOCT in solution:

The concentrations are given in equivalent sensitizer with respect to 5'-NPPOCT. As can be seen from FIG. 3, the reaction rate in the presence of one equivalent of sensitizer equals the reaction rate of the presence of 10 equivalents sensitizers, but is greater as compared to a reaction without the presence of a sensitizer and the presence of 100 equivalent of sensitizer. This means that a large excess of sensitizer causes a large decrease in the reaction rate of the cleavage (deprotection) reaction.

A non-limiting selection of labile reactive groups according to the invention, i.e. so-called "protective groups", is represented in Table 1. These compounds were prepared by syntheses known to the person skilled in the art.

TABLE 1
Labile, reactive protective groups or molecules containing such protective groups, according to the invention
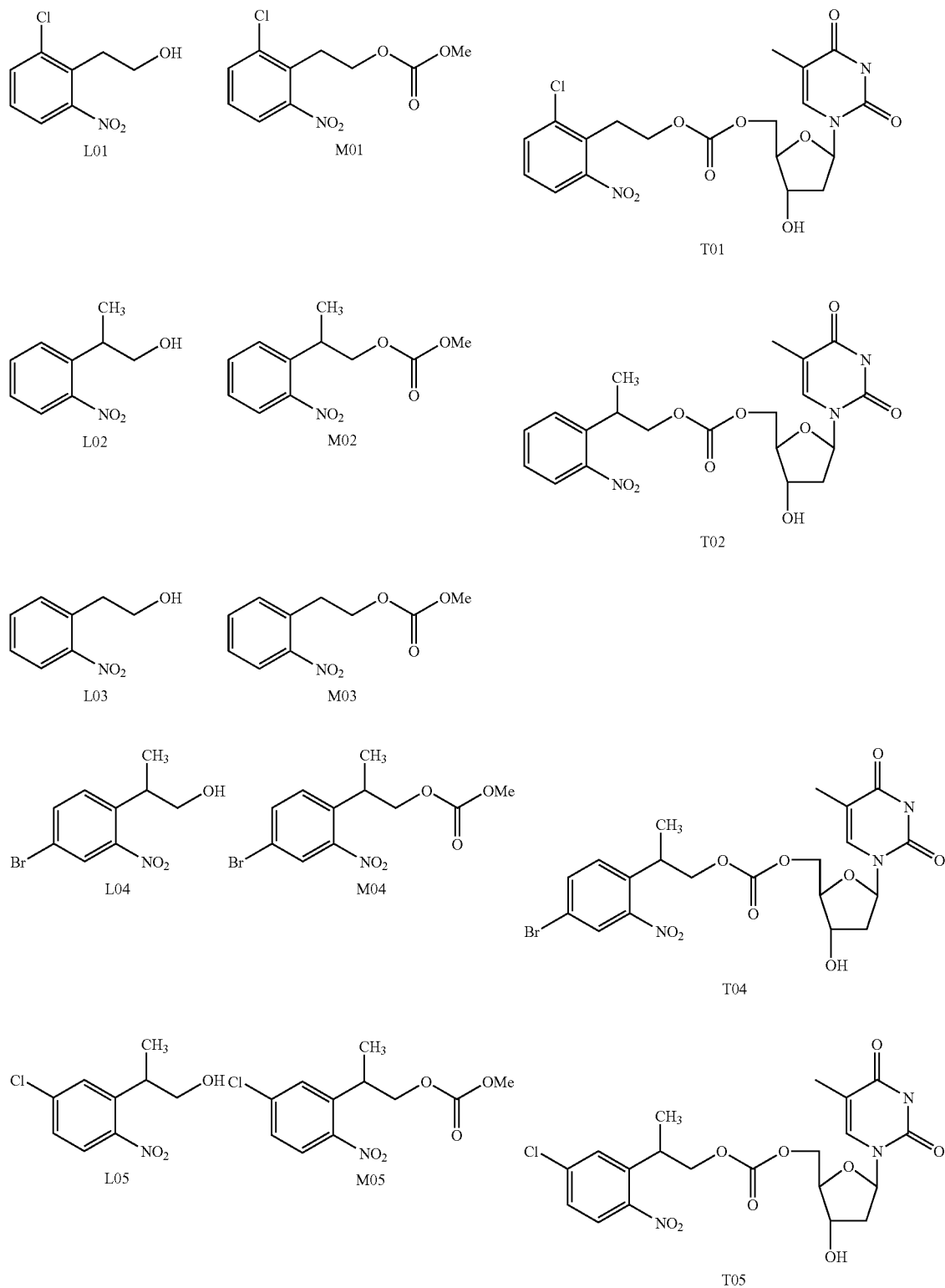

TABLE 1-continued

Labile, reactive protective groups or molecules containing such protective groups, according to the invention

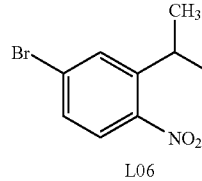

The generic names of the compounds of Table 1 are as follows:
L01 2-(2-chloro-6-nitrophenyl)ethanol
L02 2-(2-nitrophenyl)propanol
L03 2-(2-nitrophenyl)ethanol
L04 9-(4-bromo-2-nitrophenyl)propanol
L05 2-(5-chloro-2-nitrophenyl)propanol
L06 2-(5-bromo-2-nitrophenyl)propanol
L07 2-(5-iodo-2-nitrophenyl)propanol
M02-(2-chloro-6-nitrophenyl)ethyl methyl carbonate
M02 Methyl 2-(2-nitrophenyl)propyl carbonate
M03 Methyl 2-(2-nitrophenyl)ethyl carbonate
M04 2-(4-bromo-2-nitrophenyl)propyl methyl carbonate
M05 2-(5-chloro-2-nitrophenyl)propyl methyl carbonate
M06 2-(5-bromo-2-nitrophenyl)propyl methyl carbonate
M07 2-(5-iodo-2-nitrophenyl)propyl methyl carbonate
T01 2-(2-chloro-6-nitrophenyl)ethyl thymidine-5'-yl carbonate
T02 2-(2-chloro-6-nitrophenyl)ethyl thymidine-5'-yl carbonate
T04 2-(4-bromo-2-nitrophenyl)propyl thymidine-5'-yl carbonate
T05 2-(5-chloro-2-nitrophenyl)propyl thymidine-5'-yl carbonate
T06 2-(5-bromo-2-nitrophenyl)propyl thymidine-5'-yl carbonate
T07 2-(5-iodo-2-nitrophenyl)propyl thymidine-5'-yl carbonate

TABLE 2

Half lifetime rates $t_H$, photo chemical quantum yield $\phi$ and absorption coefficients $\epsilon_{365}$ of some of the compounds of Table 4

| Compound | $t_H^{(1)}$ | $\Phi$ | $\epsilon_{365}$ | $\Phi * \epsilon_{365}$ |
|---|---|---|---|---|
| 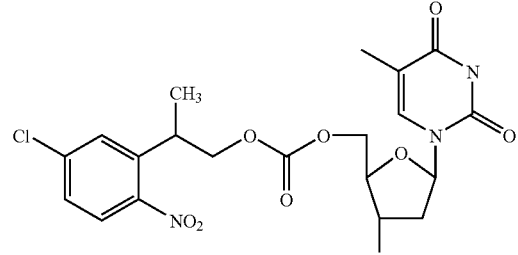 T 05 | 38 s | 0.27 | 410 | 110 |

TABLE 2-continued

Half lifetime rates $t_H$, photo chemical quantum yield $\phi$ and absorption coefficients $\epsilon_{365}$ of some of the compounds of Table 4

| Compound | $t_H^{(1)}$ | $\Phi$ | $\epsilon_{365}$ | $\Phi * \epsilon_{365}$ |
|---|---|---|---|---|
| 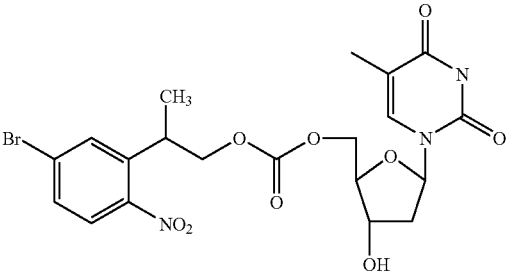 T 06 | 32 s | 0.43 | 480 | 210 |
| 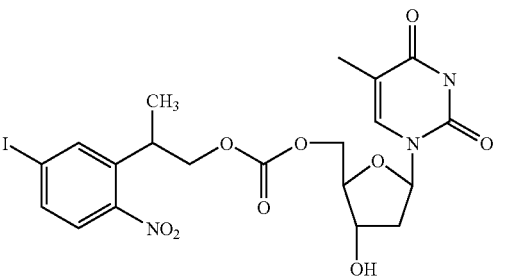 T 07 | 25 s | 0.43 | 710 | 310 |

$^{(1)}t_H$: Half lifetime

In Table 2, the rates of the cleavage reactions induced by light are characterized by means of their half lifetime rates $t_H$, and the quantum yields $\Phi$ of some of the compounds of Table 1 were determined:

The comparison of the quantum yields shows that it increases at the transition from the chlorine derivative (T 05) to the bromine derivative (T 06), but then does not increase any farther from the bromine derivative (T 06) to the iodine derivative (T 07). The first observation can be interpreted as a spin orbit-coupling effect. Said spin-orbit coupling increases with the atomic number of an element and leads to higher efficiency of the intramolecular triplet formation. This has a favorable effect on the photoreaction, since the triplet state has a longer life. The reason that the quantum yield at the transition to the iodine derivative (T 07) does not increase any further is that nearly complete triplet formation is achieved already with the bromine derivative (T 06), which can not be increased any further by an increase in spin-orbit coupling. Nevertheless, the iodine compound (T 07) has a higher sensitivity to light, which is evident from its half lifetime which is shortened again as compared to the bromine derivative (T 06). This effect may be attributed to an increase in the absorption coefficient $\epsilon$ at the selected wavelength of radiation. The overall light sensitivity is determined by the product of the light absorption capacity and the efficiency with which each absorbed photon leads to the formation of the product. Therefore, the product $\phi \times \epsilon$ of the photochemical quantum yield $\phi$ and the absorption coefficient $\epsilon$ may serve as the characteristic value of light sensitivity. Since the quantum yield cannot be increased above a value of 1, the greatest potential for improving light sensitivity lies in an increase in light absorption capacity. Electronic effects which cause a higher absorption coefficient in the case of a variation in the chemical structure of the photolabile protective group simultaneously also lead to a decrease in photoreactivity and thus in photochemical quantum yield. However, according to the invention, the effective absorption coefficient can be increased without reducing photoreactivity by using compounds which can transfer the energy of the light absorbed by them to the photolabile protective group. In this case, an energy transfer to the triplet state is advantageous, since said triplet state, as mentioned above, has a longer life and can thus more likely enter into the desired cleavage reaction.

It has been found that chemical compounds according to the invention which are suitable to carry out the methods according to the invention have the following, non-limiting characteristics:

The chemical compound according to the invention preferably absorbs at longer wavelengths than the labile protective group itself, i.e. its singlet state ($S_1$) is below the singlet state ($S_1$) of the protective group.

Further, said chemical compound has as high an absorption coefficient as possible in its longest wavelength absorption band.

The triplet state of said compound is above the triplet state of the labile protective group, and is at most energetically similar to the latter. Thus, the singlet-triplet energy gap of the sensitizer is preferably smaller than that of the labile protective group. Using nitrophenyl chromophores in the labile protective group, this energy gap is generally at about 130 kJ/mol, so that a large number of sensitizers according to the invention can be employed.

The chemical compound further has a high triplet formation quantum yield $\phi_T$, which linearly enters as a factor in sensitizing efficiency.

Further, the chemical compound has as long a triplet lifetime as possible in order to guarantee a highly efficient energy transfer. It has been found that, for a quantitative intermolecular energy transfer in a favorable energy situation of $T_1$, that a lifetime of more than 0.6 µs is sufficient, with a lifetime of more than 1 µs being particularly preferable.

The quantum yield φ of the chemical reaction according to one of the aforementioned methods of the invention upon cleavage of the labile functional group is greater than 0.5, according to particularly advantageous embodiments of the invention.

Examples of such compounds according to the invention are listed in Table 3 below.

benzo-[b]-fluorene, 5,7-dimethoxy-3-thionyl-coumarine, 1,2-cycloheptandione, 3-acetyl-6-bromo-coumarine, 2-bromo-9-acridinone, 4,4'-dibenzylbiphenyl, 2,6-dithiocaffeine, 1,4-dibromonaphthalene, dibenzo-[fg,op]-naphthalene, 10-phenyl-9-acridinone, 2-methyl-5-nitro-imidazol-1-ethanol, 1-(2-naphthoyl)-aziridine, 9-(2-naphthoyl)-carbazol, 4,6'-diamino-2-phenyl-benzooxazole, p-thiophenyl, 3-acetyl-phenanthrene, dinaphtho-[1,2-b:2', 1'-]-thiophen, (E)-piperylene, β-methyl-(E)-styrene, 2-phenyl-benzothiazol, quinoxaline, 9,9'-biphenantryl, naphtho-[1,2-c][1,2,5]-oxabiazole, phenothiazine, 2-ethoxy-naphthalene, 9-phenyl-9-stibafluorene, 9,10-antraquinone, 4,4'-dichlorodiphenyl.

TABLE 3

Chemical compounds according to the invention ("sensitizer compounds") having a higher triplet state than a photolabile protective group of molecules according to the invention

| Compound | | $E(S_1)$ kJ/mol | $\epsilon_{max}$ $M^{-1} \times cm^{-1}$ | $E(T_1)$ kJ/mol | $\phi_T$ | $\tau_T$ |
|---|---|---|---|---|---|---|
| Acridone | | n/b 304 p/nb 290 | 7580 (399 nm) | 244 252 | 0.99 <0.03(2) | 20 µs 9.2 µs |
| Xanthone | | n/b 324 p/nb | 10000 (330 nm) 6200 (335 nm) | 310 310 | | 20 ns 17.9 µs |
| Thioxanthone | | p n/b | 6800 (380 nm) | 265 | <0.88 | 73 µs 95 µs |
| 2-acetyl-naphthalene | | b p 325 | 1000 (342 nm) | 249 249 | 0.84 | 300 µs |
| Comparative compound: nitrobenzene | | n 372 p | 272 (365 nm) | 243 252 | 0.67 | 0.8 µs |

The energy (E) of the singlet and triplet states is indicated in kJ/mol. The absorption coefficient ε is indicated as $M^{-1} \times cm^{-1}$ at the respective wavelength. n refers to a non-polar solvent, p refers to a polar solvent, b is a benzene-like solvent.

τ refers to the lifetime of the triplet state in µs.

Further compounds according to the invention include, but are not limited to, N-methylacridone, 2-ethylthioxanthone, 2-anilino-naphthol, naphthalene-[1,2-c][1, 2, 5]-thiadiazole, Further compounds are evident, for example, from the book by S. L. Murov, I. Carmichael and G. L. Hug, Handbook of PhotoChemistry, Marcel Dekker, Inc., New York 1993, the disclosure of which is fully incorporated herein by reference.

Experimental Conditions:

The term "conventional conditions known to the person skilled in the art" as used hereinbefore and hereinafter, is described, for example in U.S. Pat. No. 5,763,599 or in DE 4,444,956.

UV-VIS-absorption measurements were carried out using a UV-VIS spectrometer Lambda 18 (Perkin-Elner) running under the WV Winlab software, fluorescence measurements were carried out using a luminescence spectrometer LS 50 (Perkin-Elmer) running under the FL Winlab software.

The radiation equipment consisted of a high-pressure mercury lamp (200 W), a heat filter (optical path length: 5 cm, filled with 0.3 M $CuSO_4$ solution in water), a collecting lens, an electronically controlled shutter, a 366 nm interference filter (Schott) and a temperature-controlled cell holder for light exposure cells (Hellna QS, 1 cm).

HPLC examinations were carried out using Merck-Hitachi equipment. Said equipment consisted of an L-7100 pump, an L-7200 autosampler, an L-7450A UV-diode array detector and an L-7000 interface. Merck LiChrospher 100 RP-18 (5 µm) was used as the column. Control was effected using the HSM manager on a Compaq computer.

EXAMPLES

Example 1

Reaction for Cleavage of a Labile Functional Group from a Molecule in Solution by Means of the Method According to the Invention 3 ml of a solution of thymidine derivative T02 (Table 2) (0.091 mM) and thioxanthone (0.113 mM) was pipetted into a cuvette and flushed for ca. 15 minutes with ammonia by passing the gas through the solution. Said solution was irradiated with light at a wavelength of 366 nm for different periods of time. Absorption spectra were respectively measured before and after radiation.

The solution was then flushed with nitrogen (saturated with acetonitrile) for ca. 15 minutes. Upon said nitrogen flushing, an absorption spectrum was measured again, and the solution was finally separated into its components in HPLC. These components were characterized using a UV-diode array detector.

Example 2

Preparation of DNA Chips Using the Method According to the Invention

The deprotection reaction was carried out under standard test conditions for DNA chip syntheses in a MAS 2.0 or 3.0 of Nimblegen Systems, Madison, USA. The design of the DNA chips to be prepared exhibited a standard array as usually employed in quality control tests.

There was a typical density of some 10,000 to 100,000 oligomers per $(cm)^2$, mostly present as 18-25 mers. The size or the surface area of an individual synthesis spot was 35 µm×35 µm. Said spot consisted of the image (1:1) of 4 micromirrors arranged in a square (Texas Instrument Digital Light Processor) (each mirror having an edge length of 16 µm×16 µm), each mirror being spaced apart by 1 µm.

0.01 weight-% thioxanthone was used as sensitizer, based on the solvent employed, i.e. DMSO. This resulted in a reduction of the light dose until complete cleavage of the protective group, from 7.5 $W/cm^2$, without a sensitizer molecule, to a value of 3 $W/cm^2$ at an effective lamp power of ca. 0.2-0.6 $W/cm^2$. The lamp power is independent of the MAS-type and is determined during radiation in each case.

| MAS-type | 2.0: | 1,000 Watts | Hg lamp |
| MAS-type | 3.0 | 200 Watts | Hg lamp |

Duration of the Deprotection Reaction:

| | Lamp power $W/cm^2$ | Duration (s) |
|---|---|---|
| Without thioxanthone | 0.2 | 37.5 |
| Without thioxanthone | 0.6 | 12.5 |
| With thioxanthone (0.01 weight-%) | 0.2 | 15 |
| With thioxanthone (0.01 weight-%) | 0.6 | 5 |

It is evident from the above that the addition of thioxanthone as a sensitizer leads to a considerable increase of the rate of the cleavage reaction also at low lamp powers.

The invention claimed is:

1. A method for cleavage of photolabile functional groups from molecules by the action of UV/VIS radiation which method comprises the following steps:
    a) selecting a suitable chemical compound whose triplet state is energetically very similar to the triplet state of the photolabile functional group;
    b) contacting it with the molecules comprising said photolabile functional groups,
    c) exposure to UV/VIS radiation, the sequence of steps b) and c) being optional,
    and wherein the photolabile functional group is stable at the wavelength of the UV/VIS radiation.

2. The method as claimed in claim 1, characterized in that step b) is carried out prior to step c).

3. The method as claimed in claim 1, characterized in that step c) is carried out prior to step b).

4. The method as claimed in claim 1 characterized in that step c) and step b) are carried out at the same time.

5. The method as claimed in any one of the preceding claims, characterized in that the singlet state of the chemical compound is energetically as high as or lower than the singlet state of the labile functional group.

6. The method as claimed in claim 5, characterized in that the absorption of the longest wavelength absorption band of the electromagnetic radiation of the chemical compound is at a wavelength of more than 280 nm.

7. The method as claimed in any one of claims 1-4, characterized in that the photolabile group is a photolabile protecting group.

8. A method for preparing molecular libraries containing biomolecules, in particular for preparing DNA chips, by means of spatially addressed, light-controlled synthesis from individual structural units of the biomolecules on solid substrates, which method comprises the following steps:
    a) reacting the unprotected terminal 3' or 5' hydroxy group of a nucleoside and/or of a nucleotide located on the solid substrate or of a nucleic acid analog or of the terminal amino or carboxy group of a corresponding peptide under usual conditions with a photolabile protective group, or reacting an —OH group, a substituted or unsubstituted amino or carboxy group with a structural unit comprising a photolabile protective group, and optionally purifying the reaction product,
    b) applying a chemical compound whose triplet state is energetically very similar to the triplet state of the photolabile protecting group, on the surface of the carrier comprising the nucleotides and/or nucleosides modified in step a) and/or the correspondingly modified peptides or proteins, c) irradiating, in a spatially selective manner, the surface of the carrier treated in step b), with electromagnetic radiation in the UV/VIS range;

d) reaction with a nucleoside and/or nucleotide, wherein a free 5 or 3'OH group is protected using a photolabile group and/or a corresponding peptide, which is protected by a photolabile group at the amino group or at the carboxy group; e) optionally repeating steps b) to d).

9. The method as claimed in claim 8, characterized in that the singlet state of the chemical compound is energetically as high as or lower than the singlet state of the photolabile protective group.

10. The method as claimed in claim 9, characterized in that absorption of the longest wavelength absorption band of the electromagnetic radiation of the chemical compound is at a wavelength of more than 280 nm.

11. A chemical composition, comprising a molecule having a photolabile functional group, as well as a chemical compound whose triplet state is energetically very similar to the triplet state of the photolabile functional group.

12. The chemical composition as claimed in claim 11, characterized in that the singlet state of the chemical compound is energetically as high as or lower than the singlet state of the photolabile group.

13. The chemical composition as claimed in claim 12, characterized in that the photolabile group is selected from the group consisting of NPPOC, MeNPOC, NPES NPPS MeNPPOC, PhNPPOC, DMBOC and their substituted derivatives, substituted and unsubstituted, condensed and uncondensed 2-(nitroaryl)ethoxycarbonyl or -thiocarbonyl compounds, substituted and unsubstituted, condensed and uncondensed 2-nitrobenzyl-, 2 nitrobenzyloxycarbonyl or -thiocarbonyl compounds, substituted and unsubstituted, condensed and uncondensed 2-(nitroheterocycloaryl)ethoxy-carbonyl, or -thiocarbonyl compounds, as well as substituted and unsubstituted, condensed and uncondensed 2-I (nitroheterocycloalkyl)ethoxy-carbonyl/thiocarbonyl compounds, substituted and unsubstituted 2-nitro-N-methyl aniline carbonyl- or -thiocarbonyl derivatives.

14. The chemical composition as claimed in claim 12, characterized in that the chemical compound comprises the structural motif

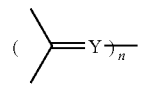

wherein Y=0 if n=0, Y=S, N, Se or Te if n=1 or 2, C is part of an aromatic, heteroaromatic or condensed aromatic or heteroaromatic system and wherein, in case n=2, the aromatic, heteroaromatic or condensed aromatic or heteroaromatic system can be the same or different.

15. The use of a chemical composition as claimed in claim 13 or 14 for the manufacture of DNA chips.

16. The chemical composition as claimed in any one of claims 11, 12, 13 or 14, characterized in that the photolabile group is a photolabile protecting group.

17. The use of a chemical composition as claimed in claim 16 for the manufacture of DNA chips.

* * * * *